United States Patent [19]

Vicario et al.

[11] Patent Number: 4,578,169
[45] Date of Patent: Mar. 25, 1986

[54] APPARATUS FOR TOTAL AND FRACTIONAL ANALYSES OF PROTEINS

[75] Inventors: Guido F. Vicario; Cesare Vicario; Ugo de Luca, all of Milan; Giuseppe Zelioli, Sant'Angelo Lodigiano, all of Italy

[73] Assignee: Elvi S.p.A., Milan, Italy

[21] Appl. No.: 620,083

[22] Filed: Jun. 12, 1984

[51] Int. Cl.⁴ ............................................ G01N 27/28
[52] U.S. Cl. ........................... 204/299 R; 204/182.7; 204/182.8; 422/55; 422/58; 422/65; 422/102
[58] Field of Search .......... 204/299 R, 180 G, 180 S, 204/182.7, 182.8; 422/55, 58, 65, 102

[56] References Cited

U.S. PATENT DOCUMENTS

| | | | |
|---|---|---|---|
| 3,047,489 | 7/1962 | Raymond | 204/299 R |
| 3,317,417 | 5/1967 | Raymond | 204/299 R |
| 3,428,547 | 2/1969 | Zec | 204/299 R |
| 3,432,414 | 3/1969 | Rand | 204/299 R |
| 3,432,424 | 3/1969 | Zec | 204/299 R |
| 3,499,360 | 3/1970 | Davis | 204/299 R |
| 3,896,021 | 7/1975 | Fosslien | 204/299 R |
| 3,915,827 | 10/1975 | Davies | 204/182.9 |
| 3,998,594 | 12/1976 | Horne | 422/65 |
| 4,043,678 | 8/1977 | Farrell et al. | 422/102 |
| 4,237,096 | 12/1980 | Popoff et al. | 422/102 |
| 4,251,159 | 2/1981 | White | 422/58 |
| 4,297,199 | 10/1981 | Hijikata | 204/299 R |
| 4,332,472 | 6/1982 | Kato et al. | 204/180 S |
| 4,391,689 | 7/1983 | Golias | 204/299 R |
| 4,427,294 | 1/1984 | Nardo | 204/299 R |

Primary Examiner—Andrew H. Metz
Assistant Examiner—B. J. Boggs, Jr.
Attorney, Agent, or Firm—Young & Thompson

[57] ABSTRACT

A planar rigid support for electrophoresis comprising a cellulose acetate strip or the like can bear on two fixed highly spongy plates which are placed in the electrolytic bath so as to emerge from the upper level thereof. In particular, the support may comprise a resilient strip-holder, in which the fastening occurs by providing in the strip two series of holes which are inserted in stakes provided on two opposite sides of the strip-holder. The several steps for the analysis of total and fractional proteins are obtained displacing each support and other fittings by a handling means preferably provided with magnetic pliers cooperating with iron portions provided on each support or fitting to be handled.

14 Claims, 21 Drawing Figures

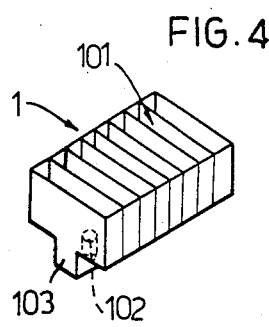
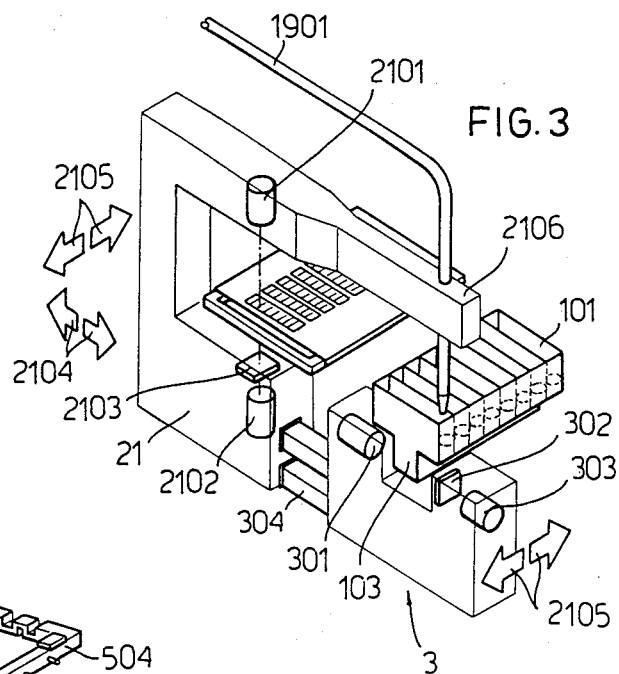
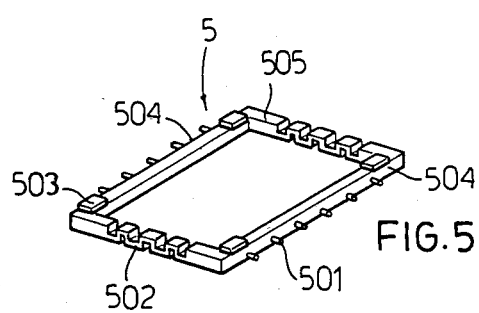
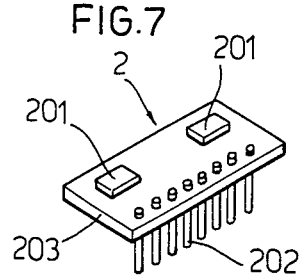
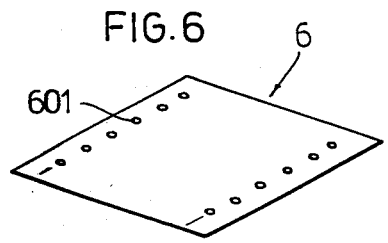
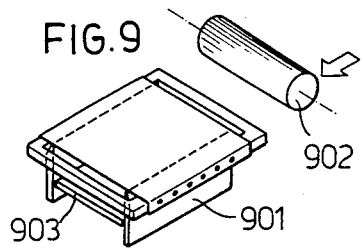
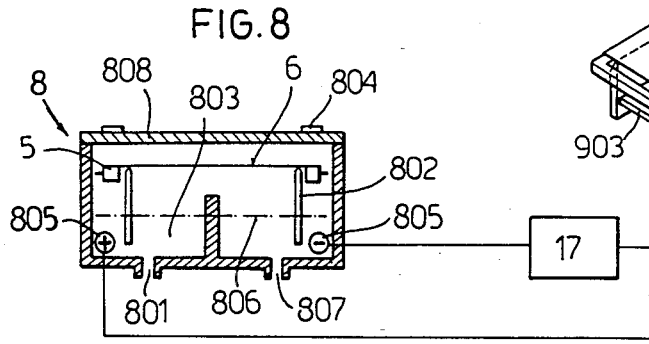

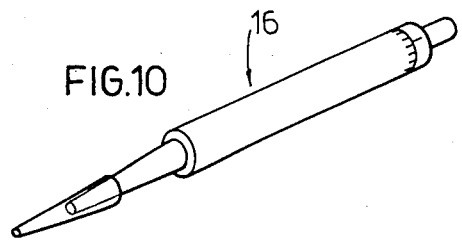
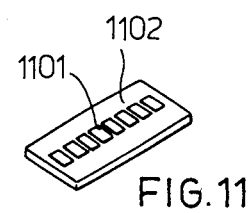
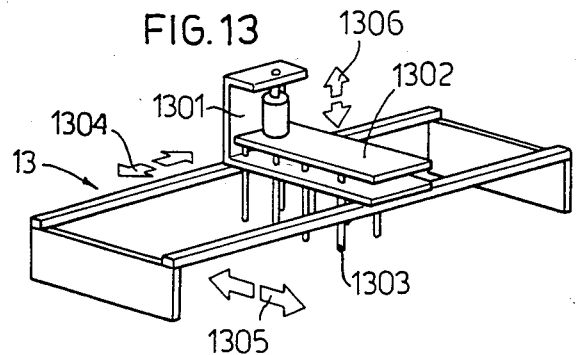
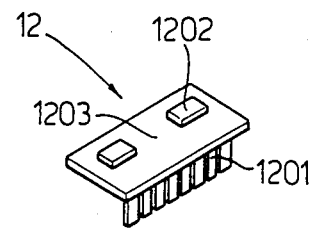
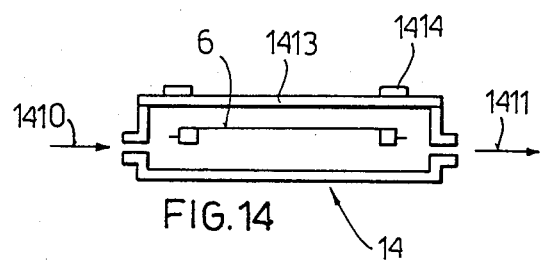
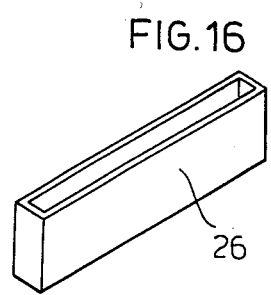
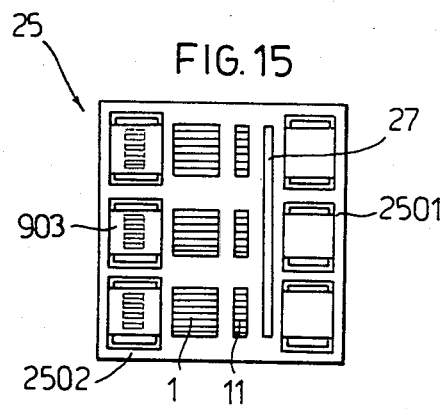
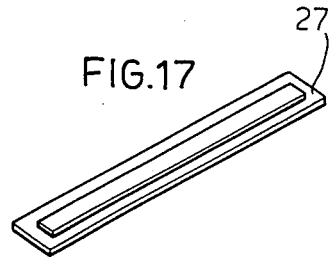

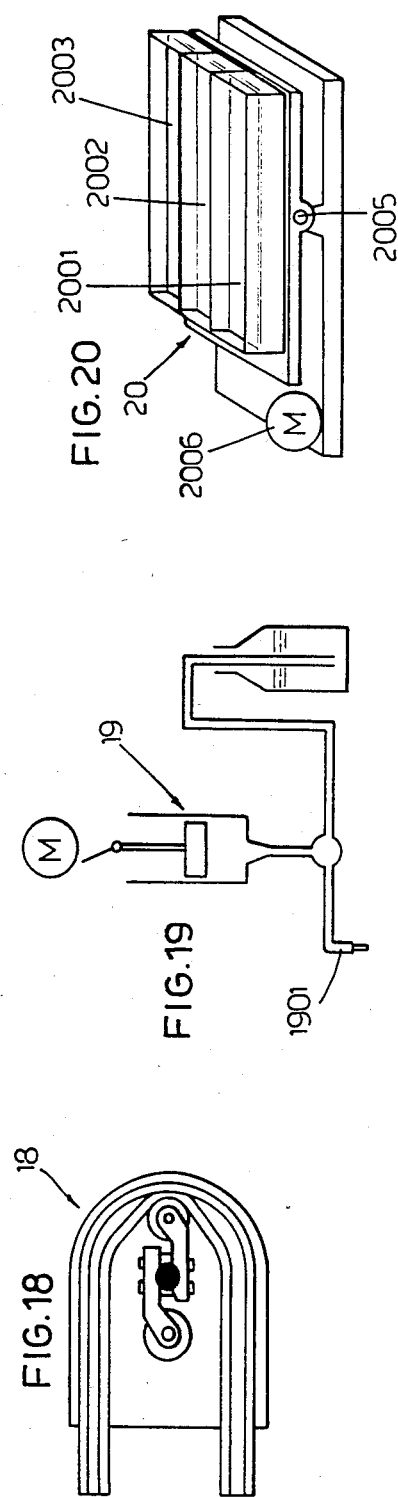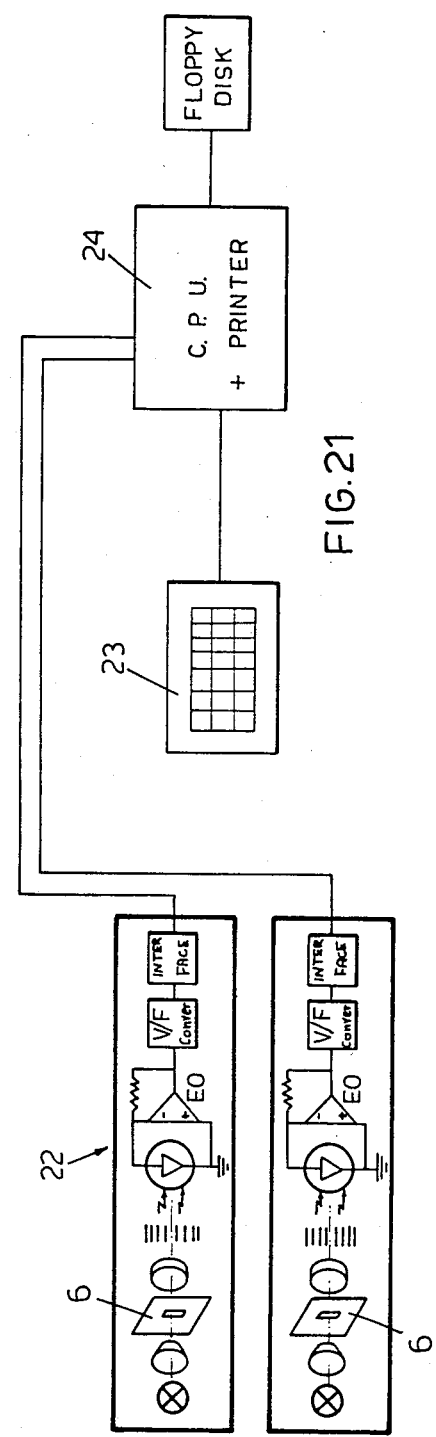

APPARATUS FOR TOTAL AND FRACTIONAL ANALYSES OF PROTEINS

This invention relates to a process and relative apparatus for processing the serum of human or animal blood, or any liquid containing proteins for obtaining analytical data relating to both total and fractional proteins.

Apparatuses are already known for obtaining the above results, but all these systems suffer from a great deal of drawbacks, require many manual operations, are slow and costly for the undue but compulsory use of large amounts of expensive chemicals. In addition, they suffer from a large possibility of errors and difficulty of reproducibility, so that an extended use of electrophoretic method is jeopardized.

Normally, electrophoresis is carried out by depositing a serum specimen and relative reactant or a cellulose acetate strip or the like and subjecting such a strip to electrolysis. This is provided by causing the folded edges of the cellulose acetate strip to penetrate into an electrolytic bath. It is well known that after electrophoresis the strip is immersed in various baths, then is read. These operations are exposed to many errors, the principal one being that caused by the heat produced by the Joule effect. In addition, these operations can hardly be automated in practice, so that the whole analysis process is still subjected to errors and is particularly of poor reproducibility.

Therefore, it is the object of the present invention to provide an apparatus for carrying out accurate, exact and reproducible analyses. Other auxiliary objects are to enable a complete automation of the whole process and a lower amount of products required for the analysis. Thus, a lower unit cost of the analyses can be provided.

The above objects have been achieved by providing the use of two highly spongy fixed plates, which are placed in the electrolytic bath so as to emerge from the latter and a planar rigid electrophoresis support comprising the cellulose acetate strip or the like which can bear on said two spongy plates.

The electrophoresis support may comprise a strip holding frame, preferably of rectangular configuration. In this case, two opposite sides are for strip clamping, while the other two sides are resilient and thereby may facilitate both the strip assembling and correct tensioning thereof during use.

Particularly, it is contemplated that strip fastening would occur by providing thereon two series of holes arranged on two opposite sides thereof, which holes are inserted on stakes in the strip-holder.

An improvement to the invention provides that the electrophoresis supports are moved by a handling means, preferably provided with magnetic pliers which cooperate with iron portions on the individual frames and on other movable fittings, if required.

Particularly, the handling means is a bridge crane.

A further improvement provides that the serum deposit zones comprise fibrous rectangles spaced apart from one another and applied to a rigid support.

A still further improvement consists of simultaneously providing more than one series of analyses. This is obtained by providing that the handling means displaces successive series of supports to the different stations.

A further improvement provides a station for colouring and washing of the electrophoretic strips.

A still further improvement of the apparatus consists of providing, if required, that the support strip is moved away by laying the latter on a support comprising two parallel spaced apart knives and causing a roller to act upon the strip, so that the strip zone between the knives falls down on a slide arranged there beneath.

A further improvement provides that the analysis specimens are inserted in a multi-cuvette comprising a series of side by side arranged cuvettes, each of which at such a distance from the adjoining cuvettes so as to maintain the existing pitch between the electrophoretic readings. Each cuvette also comprises a T-section, in which the lower transparent leg can penetrate into between two optical reading pliers (which will read the total proteins), while one of the T-branches will contain a cup of at least partially conical configuration, in which a predetermined amount of serum under examination is introduced. From this amount, a small metered fraction will be drawn for execution of the fractional proteins, then the reactant for analysis of the total proteins will be poured in the remainder. Preferably, the reactant will be first fed to the cup, then to the entire cuvette.

The invention will now be further explained with reference to an exemplary embodiment and modification thereof as shown on the accompanying drawings, in which:

FIGS. 3 to 20 are views each schematically showing in perspective view of a unit comprising the apparatus according to the invention; and FIG. 21 is the electric block diagram for the electronic control, memory and processing apparatus.

Figure 1:
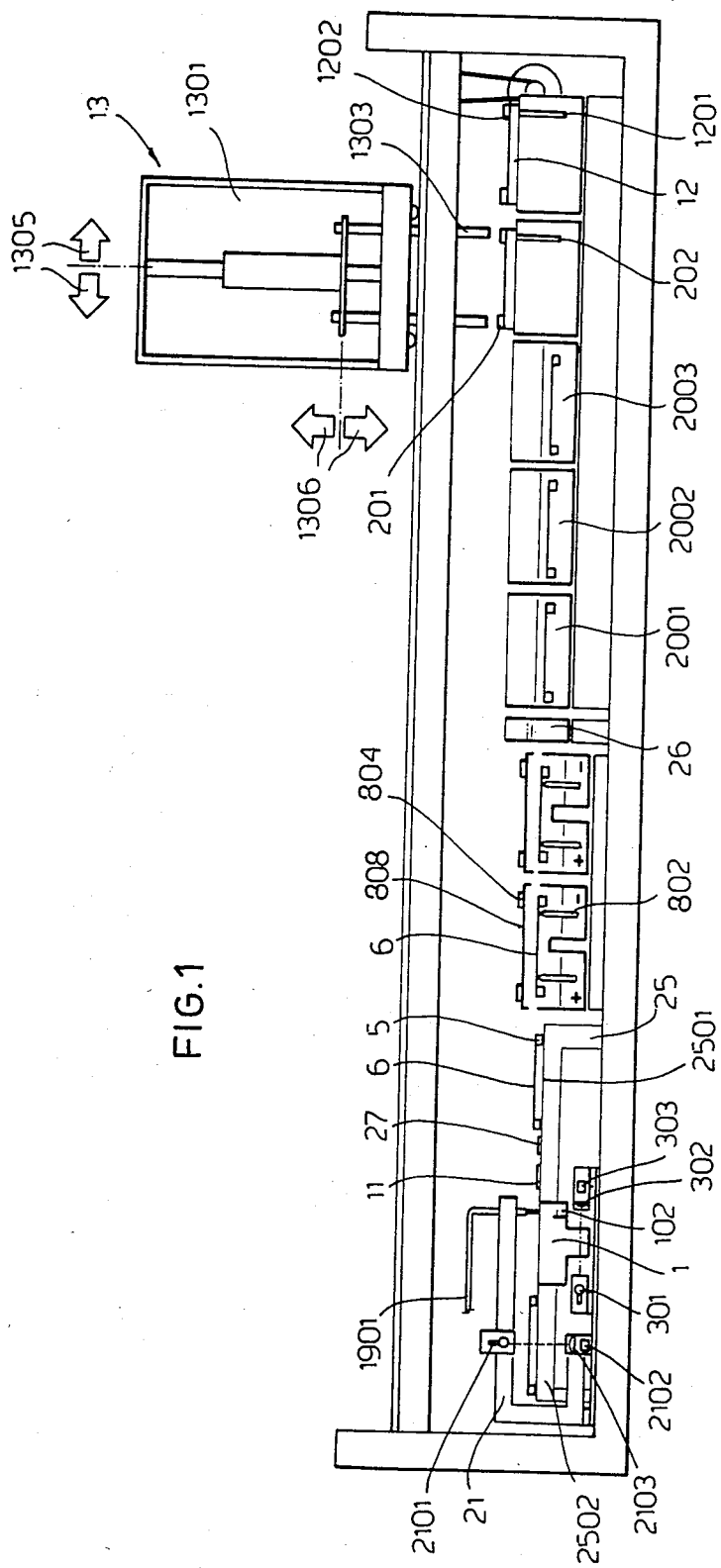
FIG. 1 is an elevational view of the apparatus as a whole.

Referring to the drawings, it will be seen that the apparatus comprises assay means comprising a multi-cuvette 1 (FIG. 4) comprising a plurality of cuvettes 101 with parallel flat faces having a T-section, the transparent lower leg of which constitutes the analysis chamber 103. There are as many cuvettes 101 as the specimens of a same series to be subjected to analysis. Each cuvette 101 houses a cylindrical-conical cup 102 of reduced volume arranged on one arm of said T-section. The distance between the middle line of two adjacent cuvettes 101 corresponds to the pitch of the electrophoretic readings.

A metered amount of serum is received in each cup 102 of each individual cuvette 101. This will be introduced by a known type of pipette 16 (FIG. 10).

A metered portion of this serum will be drawn by each capillary 202 of the serum transfer and deposit means comprising multiple withdrawal unit 2 (FIG. 7) and used for the electrophoretic deposit. The serum amount left in said cup 102 is thus known; it will be added with reactant for colorimetric metering of total proteins. At least initially the reactant is sprayed in said cup 102, then in the entire cuvette 101, thus providing for mixing the serum with the reactant. These movements are carried out by carriage 21 supporting on its arm 2106 the end of capillary 1901 (FIGS. 1, 3 and 19) from which the amount of reactant flows as metered by pump 19 (FIG. 19).

Following colour development, the multicuvette 1 will be analyzed, one cuvette 101 after the other in rapid succession by a photometric pliers 3 (FIGS. 1 and 3) essentially provided with photometric lamp 301, interferential filter 302, and optical detector 303. Pliers 3 are also mounted on carriage 21 for movement in the direction of arrow 2105, thus step by step reading the individual cuvettes 101 making up the multicuvette 1. Said carriage has also mounted thereon the device for reading the electrophoretic layouts. It comprises (see FIGS. 1 and 3) a lamp 2101, a photodetector 2102, an interferential filter 2103, a handling means 2104 for the electrophoretic reading movement and a handling means 2105 capable of transferring the device from one strip to the other. These means have been merely shown by means of arrows. The photometric pliers 3 are slidably mounted by guides 304 to move only in the direction shown by arrows 2105 scanning all of the cuvettes 101.

The apparatus for electronic processing of the two photometric signals has been denoted at 22 (FIG. 21), the keyboard for setting the patients' anagraphic data, codes and so on at 23, the computer, printer and electronic floppy discs at 24. These units provide for collection, processing and printing of the analytic values. Preferably, the photometric systems are of specialized wave length.

The multiple withdrawal unit 2 (FIG. 7), preferably disposable, consists of an elongate rigid support 203, made of plastic material, carrying a series of capillaries 202 arranged at such spacings from one another that the center distance thereof is the same as that of the cuvettes 101. This rigid support 203 is also provided with iron elements 201 intended to provide the mechanical grip for the magnetic pliers 1303 (FIG. 13) connected to the bridge crane 13. There are as many capillaries 202 as cuvettes 101 and each serve to withdraw from said cups 102 a predetermined amount of specimen intended for the electrophoretic process. Accordingly they leave in each cup 102 an amount of serum exactly corresponding to the required amount for determining the total proteins which occurs in each cuvette 101 forming part of the multicuvette 1.

This withdrawal by capillaries 202 allows the differential metering of the plasma amount required for determining the total proteins obtainable by simple addition of a dose of biuretic reactant (or the like) delivered by a known type of metering device.

FIGS. 5 and 6 show a possible embodiment for the electrophoretic support comprising a strip holder 5 (FIG. 5), preferably disposable, and made of plastic material, and a strip 6 (FIG. 6) of cellulose acetate. Said strip holder 5 essentially comprises a rectangular frame of molded plastic material, two opposite sides of which are provided with teeth or stakes 501 extending in the plane of the frame and intended to enter holes 601 provided in the proper electrophoretic strips 6 (FIG. 6). The other two sides of the strip holder are made flexible for example by a flat or fret elastic spiral 502.

Said strip holder 5 allows an extremely simplified assembling of the strip. Thus, it will suffice to bow the strip holder 5 of FIG. 5 after insertion of a series of teeth or stakes 501 in a series of holes 601, deflect the frame by taking advantage of the elasticity of spiral 502 and insert the other series of teeth in the other series of holes.

The proposed electrophoresis support avoids the use of projecting edges still used nowadays in known wet chambers for contact with the bath electrolyte. According to the present invention, two vertical spongy plates 802 having a very high absorption capability are provided in the wet chamber 8. They can be made of fiber, sponge or rigid filter paper (FIG. 8). Such plates project beyond the bath level indicated at 806 and are of such a size as to receive said strip 6, as previously mounted on the strip holder 5, entering in contact therewith a zones arranged internally of the strip holder 5. Thus, said strip 6 bears on the spongy plates 802 and absorbs the electrolyte.

It should be noted that said plates 802 are arranged internally rather than externally of the strip holder, as was the case with the projecting edges hitherto used. The distance to be travelled by the electrolyte is thus shortened and the whole analysis is facilitated. Upon arrival of said strip 6 on the spongy plates 802, the electrolyte is already at the strip bearing zone. In addition, the absorption capability of plates 802 can be very high.

Therefore, the proposed electrophoresis support minimizes the electric voltage required for migration, so as to reduce the Joule effect. This can be done by the reduction in spacing between the spongy plates 802 which are more closely arranged than the conventional edge portions drawing in the electrolyte. This reduction occurs at constant volt-centimeter gradient. By minimizing the strip heating, evaporation is reduced as well as the undesired effect of electrophoretic fraction compacting.

The strip holder 5 also solves the problem of separating the strip 6 from its strip holder 5 when the electrophoretic operations are completed. Also the strip application upon an optical slide can be achieved. To this end, the strip 6 supported by strip holder 5 is brought by magnetic pliers 1303 to bear on suitable knives 901 (FIG. 9). Through pressure of the roller 902 made of elastic material, the clear and safe cut of the central strip portion containing the electrophoretic layouts, can be obtained, the fall down of the cut strip on the underlying slide 903 and subsequent removal and elimination of said strip holder 5 by means of magnetic pliers 1303.

FIG. 8 shows the wet chamber 9 with highly absorbing vertical plates 802. These plates 802 immersed in electrolyte 803 causes the latter to arrive immediately within the two opposite sides of said strip holder 5. This chamber 8 is provided with inlet holes 801 and outlet holes 807 for electrolyte 803 allowing by suitable pumps of known type for systematic change of electrolyte at the end of every migration. The air volume in chamber 8 is highly reduced and this allows to minimize the time required for the strip under voltage to saturate said chamber with steam. A movable cover 808 provided with iron elements 804 can be moved away and brought back by means of bridge crane 13. Reference numeral 805 denotes the electrodes which are supplied through a voltage stabilizer 17.

FIG. 11 shows a multiple serum holder device 11 with raised separated fibrous zones. It comprises a plastic material support 1102 having in relief a number of fibrous zones 1101 arranged with same center distance as the multicuvette 1 (FIG. 4) and multiple withdrawal unit 2 (FIG. 7). Each relief fibrous zone 1101 is intended to receive an equal dose of serum or proteic liquid from one of capillaries 202 of the withdrawal unit 2 of FIG. 7 and be soaked up with the liquid delivered from that capillary. At due time, a multiple deposit unit 12 (FIG. 12) is caused to move down on the fibrous zones 1101 soaked with serum or liquid, said unit 12 comprising a series of deposit blades 1201 with the lower end subjected to a suitable microporous treatment, which retains the desired amount of liquid and deposits it on the electrophoretic strip 6 previously mounted in said wet chamber 8. This deposit unit 12 comprises a rigid structure 1203 fitted with a series of blades 1201 arranged at the bottom and a series of soft iron elements 1202 on the upper face. The center distance between each blade 1201 is the same as that between cuvettes 101, capillaries 202 and fibrous zones 1101.

Figure 2:
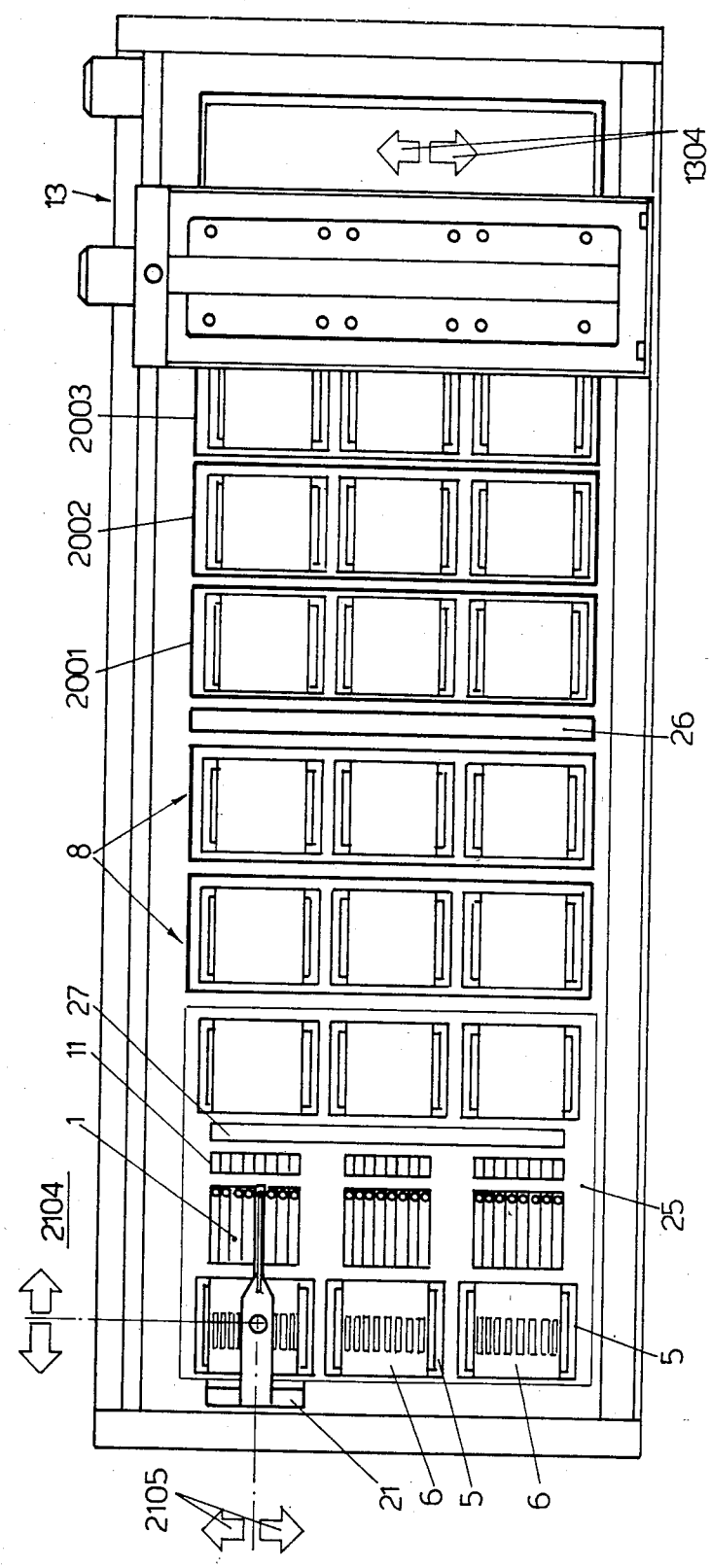
FIG. 2 is a plan view of the apparatus showwn in FIG. 1.

FIG. 13 is a view showing a transfer means comprising a bridge crane 13 which is completely similar to a miniaturized industrial bridge crane. As a whole, the bridge crane is movable transversely of the apparatus (arrows 1304, FIGS. 2 and 13) and longitudinally therealong (arrows 1305, FIGS. 1 and 13). It is also fitted with a powered latch system 1302 provided with magnetic pliers 1303. The latter are upward and downward movable in the direction of arrows 1306 (FIGS. 1 and 13). All of the vertical and horizontal movements are controlled by a computer in accordance with a program in the general software.

FIG. 14 shows a chamber 14 of laminar flow. It may be used alternatively to a standard balancing tank 2001, 2002, 2003 shown in FIG. 20. In the case of tank 14, washing is carried out by a laminar flow of liquid entering from 1410 and exiting from 1411. This chamber 14 is provided with cover 1413 also provided with iron elements 1414 for the bridge crane 13. The strip holder 5 with strip 6 mounted thereon is lapped by the laminar flow driven by a peristaltic pump 18 of known type (FIG. 18). The chamber 14 affords a higher efficiency both in colouring and decolorization, as well as application to the strip of special substances (reactive layers, immunological layers, culture soils or the like). Washing action is improved or enhanced by continuous passage of fresh liquid. There is also an enormous saving in reactants for the colouring and washing steps and possibility of applying and recovering of costly liquids and reactants, by admission thereof into said laminar flow chamber and subsequent withdrawal thereof.

FIG. 20 shows the stirrer unit 20 comprising a motor 2006 stirring the three balancing tanks 2001, 2002, 2003, containing dyes and decolorants, which are mounted on a pin 2005.

The extractable box 25 (FIGS. 1 and 15) allows the loading and extraction of the material being examined. It comprises a bearing plane 2501, having mounted thereon the slides 903 carrying the strips 6 to be cut and cut, the heat zone 2502, the serum holder device 11 and the drying filter of the depositing device 27 (FIG. 17), as well as the multicuvette 1. The cut occurs on said box 25 at the heat zone 2502. A washing basin 26 (FIGS. 2 and 16) for the deposit blades 1201 is also provided in the apparatus.

The principle of operation for the apparatus is as follows:

A series of serum specimens are introduced in controlled and sufficient amount for analysis of total and fractional proteins, one specimen after the other, by means of a single or multiple automatic micropipette 16 into a series of cups 102, each of which placed within a series of cuvettes 101 of a multicuvette 1. A series of capillaries 202 withdraw from each cup 102 a constant fixed amount of serum sufficient for analysis of fractional proteins, leaving in the cup the required and sufficient amount of serum for analysis of total proteins.

The withdrawal unit 2, being provided with iron elements 201, allows by means of magnetic pliers 1303 the lifting thereof from the bridge crane 13, and transfer thereof first to cups 102 and then on the multiple serum holder device 11 having raised fibrous zones 1101 on which the serum in capillaries 202 is discharged.

After withdrawal by capillaries 202, said multicuvette 1 is flooded by a determined volume of reactant delivered through capillary 1901 by metering pump 19. This reactant feeding capillary 1901 causes the specimen to exit from the cup 102 and provides for mixing thereof within cuvette 101. To this purpose, the reactant is first directed to the center of cup 102, then to the zone 103 of each cuvette. This is a possible because said capillary 1901 is mounted on arm 2106 of carriage 21 moving in the direction of arrows 2104. During this movement, the photometric pliers 3, mounted on sliding guides 304, do not move in this direction. As the reactant has been poured in a cuvette 101, the capillary 1901 is displaced by one step in the next cuvette due to carriage 21 now moving in the direction of arrows 2105. In this case, said displacement will be carried out by said photometric pliers 3.

At the end of the reaction, said photometric pliers 3 (FIGS. 1 and 3) will scan each compartment 103 by means of lamp 301, filter 302 and optical sensor 303.

A strip holder 5 is placed on bearing plane 2501 with a mounted strip 6, so that teeth 501 are inserted in the holes 601 of the strip.

The bridge crane 13 withdraws the cover 808 of one of the wet chambers 8 by means of the iron elements 804 and overlaps it onto the cover 808 of the adjacent chamber.

Then, said bridge crane 13 withdraws said strip holder 5 with the mounted strip 6 and lays it on the vertical spongy plates 802.

Now, the bridge crane 13 withdraws the multiple deposit unit 12 by means of the iron elements 1202, carrying it on the multiple serum holder device 11 with raised fibrous zones 1101 and by means of deposit blades 1201 withdraws the serum of which the zones are soaked.

Then, said bridge crane 13 carries the multiple deposit unit 12 onto the strip 6 already mounted in chamber 8 and lays down the specimens by means of blades 1201. Whereupon, the unit 12 is moved back to storage and cover 808 is placed on wet chamber 8, the buffer solution is introduced by pump 18, the voltage from feeder 17 is applied to electrodes 805 to complete migration.

Upon migration achievement, cover 808 is opened again by the bridge crane 13 and superimposed again to the cover of the adjacent chamber.

The bridge crane 13 withdraws the strip holder 5 with mounted strip 6 from wet chamber 8, in which protein fractioning has already occurred, transfers it to the first basin 2001 for colouring, then takes it again for transfer to the second tank 2002 for decoloration and finally to the third tank 2003 for last and final decoloration. A balancing system shown in FIG. 20 facilitates colouring and decoloration. Alternatively, all of the colouring and decoloration steps can be carried out in the laminar flow chamber 14.

Now, said strip holder 5 with mounted strip 6, on which protein fractioning, colouring and decoloration steps have been carried out, is brought from bridge crane 13 onto the heat zone 2502 of box 25 (FIGS. 15 and 1).

Here, the strip is cut (FIG. 9) by the combined action of knives 901 and roller 902, so as to fall down on the underlying slide 903 and is rolled thereon and made adherent to roller 902, for separation from strip holder 5 which is then moved away from bridge crane 13.

Below slide 903, through a suitable opening in heat zone 2502, first a hot air flow will be provided to accelerate the diaphanization of strip 6 and then the passage of monochromatic light from lamp 2101 mounted on the reading carriage of the electrophoretic layouts 21, intended to fall down on the optical sensor 2102 through the interferential filter 2103.

The reading carriage 21 carries out the required displacements, being mounted for displacement in the direction 2104 for reading of the fractional proteins and in the direction 2015 for displacement from one layout to the other.

During movement 2104 the photometric data collected or picked up by device 22 will be supplied to processor 24 and then transferred to the printer.

The computer, having previously stored the anagraphic patient's data from the keyboard 23 operated by the operator, the total protein data from the photometric pliers 3 and finally the fractional protein data from system 21, provides for processing, ordering and printing the analitycal values in clinically valid form.

At the end of operations, the deposit blades 1201 are washed in washing basin 26 and dried in 27, still owing to the transport movements of bridge crane 13.

What we claim is:

1. In an automated electrophoresis apparatus for analysis of a protein-containing serum having assay means, at least one electrophoresis chamber, at least one support for electrophoresis, at least one strip of cellulose acetate, means for cutting and separating from said support said at least one strip, a first means for transferring said at least one strip between a storage position and a position in said chamber, and a subsequent cutting position, and serum depositing means for depositing serum in an intermediate position between said assay means and said electrophoresis chamber; the improvement comprising an electrophoresis chamber having at least one electrolytic bath and an electrophoresis support including at least one strip of cellulose acetate, said chamber further comprising two highly spongy fixed plates arranged in the electrolytic bath to emerge therefrom and a planar rigid electrophoresis support for bearing on the two spongy plates, said planar rigid support comprising a strip holder frame on two opposite sides of which said strip of cellulose acetate is secured.

2. An apparatus as claimed in claim 1, wherein said electrophoresis support is provided with magnetic elements cooperating with magnetic elements on the transfer means.

3. An apparatus as claimed in claim 1, wherein said transfer means comprises a bridge crane.

4. An apparatus as claimed in claim 1, wherein said strip holder frame has at least two opposite flexible sides.

5. An apparatus as claimed in claim 1, said cutting and separating means comprising two knives and a pressure roller for cutting and separation of said strip from said strip holder.

6. An apparatus as claimed in claim 1, wherein said assay means comprises side-by-side cuvettes of T-section comprising an interior cup, a transparent leg which is used for photometric reading, and at least one arm providing a support for said interior cup.

7. An apparatus according to claim 1, comprising serum depositing means provided with side-by-side raised fibrous receivers.

8. An apparatus as claimed in claim 1, wherein the assay means, transfer means, and serum depositing means all comprise equidistantly spaced elements.

9. An apparatus for electrophoretic analysis of proteins having at least an electrolytic bath and an electrophoresis support including at least a strip of cellulose acetate, which apparatus comprises:
   (A) a device for photometric determination of the total proteins in a cuvette (1) having a T shape section the lower portion (103) of which is transparent and
   (B) a device for electrophoretic determination of the fractional proteins having two highly spongy fixed plates (802) arranged in the electrolytic bath (803) and emerging therefrom and a planar rigid support for electrophoresis which comprises at least a strip holder frame (5) on which a strip (6) of cellulouse acetate is secured, said strip with its lower side resting on both plates (802),
   the devices (A) and (B) being joined in the apparatus so that between the cuvette and electrolytic bath a withdrawal capillary (802), a deposit blade (1201) and a deposit surface (1101) are provided for the serum.

10. An apparatus according to claim 9, wherein a plurality of cuvettes are joined together in a row so as to form a series of cuvettes, whereas in each cuvette (101) a basis (102) is provided.

11. An apparatus according to claim 9, wherein the strip holder frame (5) is provided with magnetic fasteners (804) which can be lifted by counter fasteners (1303).

12. An apparatus according to claim 9, wherein the strip holder frame (5) has at least two opposite flexible sides.

13. An apparatus according to claim 9, wherein the deposit surface for the serum comprises raised fibrous serum receivers (1101) arranged spaced apart one from the other and on a rigid support (1102).

14. An apparatus according to claim 13, wherein the cuvettes (101) in the plurality of cuvettes, the deposit blades (1201), the fibrous zones (1101) and the withdrawal capillaries (202) are all arranged at the same axial distance.

* * * * *